United States Patent [19]

Huse

[11] Patent Number: 5,523,388
[45] Date of Patent: Jun. 4, 1996

[54] METHODS OF SYNTHESIZING OLIGONUCLEOTIDES WITH RANDOM CODONS

[75] Inventor: William D. Huse, Del Mar, Calif.

[73] Assignee: Ixsys, Inc., San Diego, Calif.

[21] Appl. No.: 396,346

[22] Filed: Feb. 27, 1995

Related U.S. Application Data

[63] Continuation of Ser. No. 71,473, Jun. 4, 1993, abandoned, which is a continuation of Ser. No. 990,355, Dec. 14, 1992, Pat. No. 5,264,563, which is a continuation of Ser. No. 573,648, Aug. 24, 1990, abandoned.

[51] Int. Cl.$^6$ ............................ C07H 21/02; C07H 21/04
[52] U.S. Cl. .................. 536/22.1; 536/25.3; 536/25.31; 536/25.33; 536/25.34
[58] Field of Search .................... 536/22.1, 25.3, 536/25.31, 25.33, 25.34

[56] References Cited

U.S. PATENT DOCUMENTS

| | | | |
|---|---|---|---|
| 4,458,066 | 7/1984 | Caruthers et al. | 536/27 |
| 4,500,707 | 2/1985 | Caruthers et al. | 536/25.3 |
| 5,082,767 | 1/1992 | Hatfield et al. | 435/6 |
| 5,264,563 | 11/1993 | Huse | 536/25.3 |

FOREIGN PATENT DOCUMENTS

| | | |
|---|---|---|
| 383620 | 2/1990 | European Pat. Off. . |

OTHER PUBLICATIONS

Cwirla, Steven E. et al., "Peptides on phage: A Vast Library of Peptides for Identifying Ligands." Proc. Natl. Acad. Sci. USA. 87:6378–6382.

Devlin, James J. et al., "Random Peptide Libraries: A Source of Specific Protein Binding Molecules." Science 249:404–406 (1990).

Scott, Jamie K. and Smith, George P. "Searching for Peptide Ligands with an Epitope Library." Science 249:386–390 (1990).

Blake, R. D. et al. "Tuplet Analysis of Sequences." Federation Proceedings—Abstracts. Indexes #2958. (1983).

Adams, Roger L. et al. *The Biochemistry of the Nucleic Acids.* Publisher: Chapman and Hall, London and New York. pp. 11–12 (1986).

*Primary Examiner*—W. Gary Jones
*Assistant Examiner*—Eggerton Campbell
*Attorney, Agent, or Firm*—Campbell and Flores

[57] ABSTRACT

The invention provides a method of synthesizing oligonucleotides having random tuplets using individual monomers. The steps consist of: (1) sequentially coupling monomers on separate supports to form at least two different tuplets, the coupling is performed in separate reaction vessels; (2) mixing the supports from the reaction vessels; (3) dividing the mixed supports into two or more separate reaction vessels; and (4) repeating steps (1) through (3) one or more times in the reaction vessels of step (3), wherein the last step ends at step (2). Additionally, the oligonucleotides can be cleaved from the supports.

20 Claims, 2 Drawing Sheets

METHODS OF SYNTHESIZING OLIGONUCLEOTIDES WITH RANDOM CODONS

This application is a continuation of application Ser. No. 08/071,1473, filed on Jun. 4, 1993, which is abandoned, which is a continuation of application Ser. No. 07/990,355, filed on Dec. 14, 1992 (U.S. Pat. No. 5,264,563), which is a continuation of Ser. No. 07/573,648, filed on Aug. 24, 1990, which is abandoned.

BACKGROUND OF THE INVENTION

This invention relates generally to oligonucleotide synthesis and, more particularly, to methods of synthesizing oligonucleotides having random codons using individual monomers.

The speed and availability of automated nucleic acid synthesis has led to rapid technological advances in biological research. For example, the availability of synthetic primers for sequencing has permitted researchers to decrease their time and labor involved in sequencing a particular nucleic acid by approximately sixty percent. Another technology which is facilitated by synthetic oligonucleotides is the polymerase chain reaction (PCR). This technique, which involves the exponential amplification of sequences between two synthetic primers, offers unprecedented detection levels and permits genetic manipulation of the amplified sequence. Further, the availability of synthetic primers allows a variety of genetic manipulations to be performed with relatively simple procedures, including site-specific mutagenesis and the custom design of genetic vectors.

Sequences to be cloned are also routinely modified with synthetic oligonucleotides. The modifications of either vector or insert sequence can range from the addition of a simple sequence encoding a restriction enzyme site to more complicated schemes involving modifying the translation product of the cloned sequence with a specific peptide or a variety of peptide sequences. Thus, these technological advances associated with synthetic oligonucleotides has afforded researchers many opportunities to study diverse biological phenomenon in greater detail and with greater speed and accuracy.

Oligonucleotide synthesis proceeds via linear coupling of individual monomers in a stepwise reaction. The reactions are generally performed on a solid phase support by first coupling the 3' end of the first monomer to the support. The second monomer is added to the 5' end of the first monomer in a condensation reaction to yield a dinucleotide coupled to the solid support. At the end of each coupling reaction, the by-products and unreacted, free monomers are washed away so that the starting material for the next round of synthesis is the pure oligonucleotide attached to the support. In this reaction scheme, the stepwise addition of individual monomers to a single, growing end of a oligonucleotide ensures accurate synthesis of the desired sequence. Moreover, unwanted side reactions are eliminated, such as the condensation of two oligonucleotides, resulting in high product yields.

In some instances, it is desired that synthetic oligonucleotides have random nucleotide sequences. This result can be accomplished by adding equal proportions of all four nucleotides in the monomer coupling reactions, leading to the random incorporation of all nucleotides and yields a population of oligonucleotides with random sequences. Since all possible combinations of nucleotide sequences are represented within the population, all possible codon triplets will also be represented. If the objective is ultimately to generate random peptide products, this approach has a severe limitation because the random codons synthesized will bias the amino acids incorporated during translation of the DNA by the cell into polypeptides.

The bias is due to the redundancy of the genetic code. There are four nucleotide monomers which leads to sixty-four possible triplet codons. With only twenty amino acids to specify, many of the amino acids are encoded by multiple codons. Therefore, a population of oligonucleotides synthesized by sequential addition of monomers from a random population will not encode peptides whose amino acid sequence represents all possible combinations of the twenty different amino acids in equal proportions. That is, the frequency of amino acids incorporated into polypeptides will be biased toward those amino acids which are specified by multiple codons.

To alleviate amino acid bias due to the redundancy of the genetic code, the oligonucleotides can be synthesized from nucleotide triplets. Here, a triplet coding for each of the twenty amino acids is synthesized from individual monomers. Once synthesized, the triplets are used in the coupling reactions instead of individual monomers. By mixing equal proportions of the triplets, synthesis of oligonucleotides with random codons can be accomplished. However, the cost of synthesis from such triplets far exceeds that of synthesis from individual monomers because triplets are not commercially available.

There thus exists a need for a method to synthesize oligonucleotides with random codons which alleviates genetic redundancy incurred through present synthesis methods using individual monomers and does not have the prohibitive costs associated with methods using pre-synthesized triplets. The present invention satisfies these needs and provides additional advantages as well.

SUMMARY OF THE INVENTION

The invention provides a method of synthesizing oligonucleotides having random tuplets using individual monomers. The steps consist of: sequentially coupling monomers on separate supports to form at least two different tuplets, the coupling is performed in separate reaction vessels; mixing the supports from the reaction vessels; dividing the mixed supports into two or more separate reaction vessels; and repeating the coupling, mixing and dividing steps one or more times in the reaction vessels, ending with a mixing or dividing step. Additionally, the oligonucleotides can be cleaved from the supports.

DETAILED DESCRIPTION OF THE INVENTION

Figure 1:
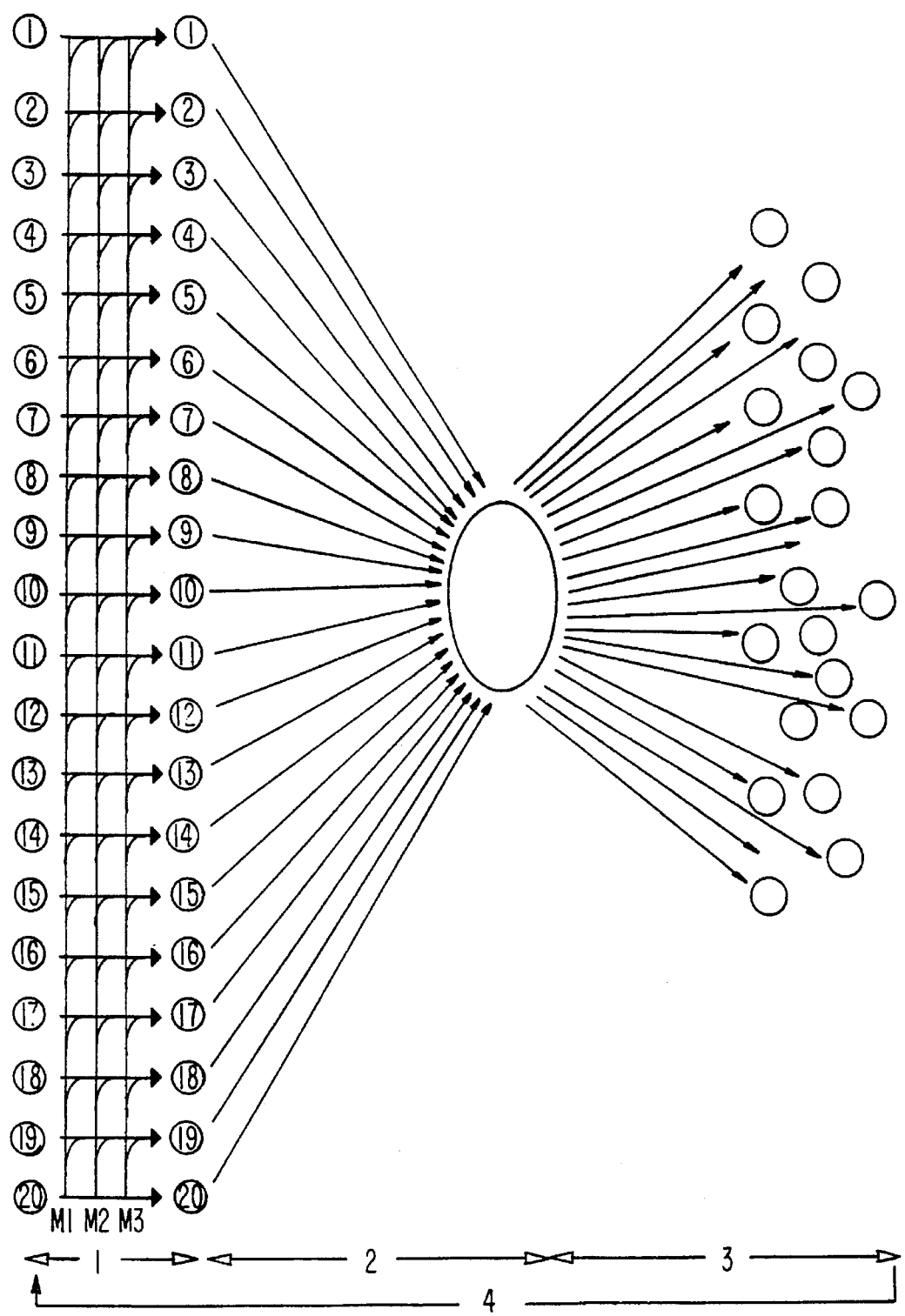
FIG. 1 is a schematic drawing for synthesizing oligonucleotides from nucleotide monomers with random tuplets at each position using twenty reaction vessels.

This invention is directed to a simple and inexpensive method for synthesizing oligonucleotides having random tuplets using individual monomers. The method is advantageous in that individual monomers are used instead of tuplets. The monomers are commercially available in a form which can be used in oligonucleotide synthesis and are inexpensive. An additional advantage of the method is that it can alleviate codon redundancy inherent in present methods of random synthesis by utilizing only a non-degenerate subset of all triplets. Thus, the method is able to produce a large proportion of possible oligonucleotides with random tuplets. The oligonucleotides produced are useful for making an unlimited number of pharmacological and research products.

In a preferred embodiment, the invention entails the sequential coupling of monomers to produce oligonucleotides with random codons. The coupling reactions for the randomization of twenty codons which specify the amino acids of the genetic code are performed in ten different reaction vessels. Each reaction vessel contains a support on which the monomers for two different codons are coupled in three sequential reactions. One of the reactions couple an equal mixture of two monomers such that the final product has a sequence of two different codons. The codons are randomized by removing the supports from the reaction vessels and mixing them to produce a single batch of supports containing all twenty codons. Synthesis at the next codon position proceeds by equally dividing the mixed batch of supports into ten reaction vessels as before and sequentially coupling the monomers for each pair of codons. The supports are again mixed to randomize the codons at the position just synthesized. The cycle of coupling, mixing and dividing continues until the desired number of codon positions have been randomized. After the last position has been randomized, the oligonucleotides with random codons are cleaved from the support.

As used herein, the term "monomer" or "nucleotide monomer" refers to individual nucleotides used in the chemical synthesis of oligonucleotides. Monomers that can be used include both the ribo- and deoxyribo- forms of each of the five standard nucleotides (derived from the bases adenine (A or dA, respectively), guanine (G or dG), cytosine (C or dC), thymine (T) and uracil (U)). Derivatives and precursors of bases such as inosine which are capable of supporting polypeptide biosynthesis are also included as monomers. Also included are chemically modified nucleotides, for example, one having a reversible blocking agent attached to any of the positions on the purine or pyrimidine bases, the ribose or deoxyribose sugar or the phosphate or hydroxyl moieties of the monomer. Such blocking groups include, for example, dimethoxytrityl, benzoyl, isobutyryl, beta-cyanoethyl and diisopropylamine groups, and are used to protect hydroxyls, exocyclic amines and phosphate moieties. Other blocking agents can also be used and are known to one skilled in the art.

As used herein, the term "tuplet" refers to a group of elements of a definable size. The elements of a tuplet as used herein are nucleotide monomers. For example, a tuplet can be a dinucleotide, a trinucleotide or can also be four or more nucleotides.

As used herein, the term "codon" or "triplet" refers to a tuplet consisting of three adjacent nucleotide monomers which specify one of the twenty naturally occurring amino acids found in polypeptide biosynthesis. The term also includes nonsense codons which do not specify any amino acid.

"Random codons" or "randomized codons," as used herein, refers to more than one codon at a position within a collection of oligonucleotides. The number of different codons can be from two to twenty at any particular position.

"Randomized oligonucleotides," as used herein, refers to a collection of oligonucleotides with random codons at one or more positions. For example, if the randomized oligonucleotides are six nucleotides in length (i.e., two codons) and both the first and second codon positions are randomized to encode all twenty amino acids, then a population of oligonucleotides with every possible combination of the twenty triplets in the first and second position makes up the above population of randomized oligonucleotides. The number of possible codon combinations is $20^2$. Likewise, if randomized oligonucleotides of fifteen nucleotides in length are synthesized which are randomized at all positions, then all triplets coding for each of the twenty amino acids will be found in equal proportions at every position. The population constituting the randomized oligonucleotides will contain $20^{15}$ different possible species of oligonucleotides. "Random tuplets," or "randomized tuplets" are defined analogously.

As used herein, the term "support" refers to a solid phase material for attaching monomers for chemical synthesis. Such support is usually composed of materials such as beads of control pore glass but can be other materials known to one skilled in the art. The term is also meant to include one or more monomers coupled to the support for additional oligonucleotide synthesis reactions.

As used herein, the terms "coupling" or "condensing" refers to the chemical reactions for attaching one monomer to a second monomer or to a solid support. Such reactions are known to one skilled in the art and are typically performed on an automated DNA synthesizer such as a MilliGen/Biosearch Cyclone Plus Synthesizer using procedures recommended by the manufacturer. "Sequentially coupling" as used herein, refers to the stepwise addition of monomers.

The invention provides a method of synthesizing oligonucleotides having random tuplets using individual monomers. The method comprises several steps, the first being synthesis of a nucleotide tuplet for each tuplet to be randomized. As described here and below, a nucleotide triplet (i.e., a codon) will be used as a specific example of a tuplet. Any size tuplet will work using the methods disclosed herein, and one skilled in the art would know how to use the methods to randomize tuplets of any size.

If the randomization of codons specifying all twenty amino acids is desired at a position, then twenty different codons are synthesized. Likewise, if randomization of only ten codons at a particular position is desired then those ten codons are synthesized. Randomization of codons from two to sixty-four can be accomplished by synthesizing each desired triplet. Preferably, randomization of from two to twenty codons is used for any one position because of the redundancy of the genetic code. The codons selected at one position do not have to be the same codons selected at the next position. Additionally, the sense or anti-sense sequence oligonucleotide can be synthesized. The process therefore provides for randomization of any desired codon position with any number of codons.

Codons to be randomized are synthesized sequentially by coupling the first monomer of each codon to separate supports. The supports for the synthesis of each codon can, for example, be contained in different reaction vessels such that one reaction vessel corresponds to the monomer coupling reactions for one codon. As will be used here and below, if twenty codons are to be randomized, then twenty reaction vessels can be used in independent coupling reactions for the first twenty monomers of each codon. Synthesis proceeds by sequentially coupling the second monomer of each codon to the first monomer to produce a dimer, followed by coupling the third monomer for each codon to each of the above-synthesized dimers to produce a trimer (FIG. 1, step 1, where $M_1$, $M_2$ and $M_3$ represent the first, second and third monomer, respectively, for each codon to be randomized).

Following synthesis of the first codons from individual monomers, the randomization is achieved by mixing the supports from all twenty reaction vessels which contain the individual codons to be randomized. The solid phase support can be removed from its vessel and mixed to achieve a random distribution of all codon species within the population (FIG. 1, step 2). The mixed population of supports, constituting all codon species, are then redistributed into twenty independent reaction vessels (FIG. 1, step 3). The resultant vessels are all identical and contain equal portions of all twenty codons coupled to a solid phase support.

For randomization of the second position codon, synthesis of twenty additional codons is performed in each of the twenty reaction vessels produced in step 3 as the condensing substrates of step 1 (FIG. 1, step 4). Steps 1 and 4 are therefore equivalent except that step 4 uses the supports produced by the previous synthesis cycle (steps 1 through 3) for codon synthesis whereas step 1 is the initial synthesis of the first codon in the oligonucleotide. The supports resulting from step 4 will each have two codons attached to them (i.e., a hexanucleotide) with the codon at the first position being any one of twenty possible codons (i.e., random) and the codon at the second position being one of the twenty possible codons.

For randomization of the codon at the second position and synthesis of the third position codon, steps 2 through 4 are again repeated. This process yields in each vessel a three codon oligonucleotide (i.e., 9 nucleotides) with codon positions 1 and 2 randomized and position three containing one of the twenty possible codons. Steps 2 through 4 are repeated to randomize the third position codon and synthesize the codon at the next position. The process is continued until an oligonucleotide of the desired length is achieved. After the final randomization step, the oligonucleotide can be cleaved from the supports and isolated by methods known to one skilled in the art. Alternatively, the oligonucleotides can remain on the supports for use in methods employing probe hybridization.

The diversity of codon sequences, i.e., the number of different possible oligonucleotides, which can be obtained using the methods of the present invention, is extremely large and only limited by the physical characteristics of available materials. For example, a support composed of beads of about 100 µm in diameter will be limited to about 10,000 beads/reaction vessel using a 1 µM reaction vessel containing 25 mg of beads. This size bead can support about $1 \times 10^7$ oligonucleotides per bead. Synthesis using separate reaction vessels for each of the twenty amino acids will produce beads in which all the oligonucleotides attached to an individual bead are identical. The diversity which can be obtained under these conditions is approximately $10^7$ copies of 10,000×20 or 200,000 different random oligonucleotides. The diversity can be increased, however, in several ways without departing from the basic methods disclosed herein. For example, the number of possible sequences can be increased by decreasing the size of the individual beads which make up the support. A bead of about 30 µm in diameter will increase the number of beads per reaction vessel and therefore the number of oligonucleotides synthesized. Another way to increase the diversity of oligonucleotides with random codons is to increase the volume of the reaction vessel. For example, using the same size bead, a larger volume can contain a greater number of beads than a smaller vessel and therefore support the synthesis of a greater number of oligonucleotides. Increasing the number of codons coupled to a support in a single reaction vessel also increases the diversity of the random oligonucleotides. The total diversity will be the number of codons coupled per vessel raised to the number of codon positions synthesized. For example, using ten reaction vessels, each synthesizing two codons to randomize a total of twenty codons, the number of different oligonucleotides of ten codons in length per 100 µm bead can be increased where each bead will contain about $2^{10}$ or $1\times10^3$ different sequences instead of one. One skilled in the art will know how to modify such parameters to increase the diversity of oligonucleotides with random codons.

The invention provides for a method of synthesizing oligonucleotides having random codons at each position using individual monomers wherein the number of reaction vessels is less than the number of codons to be randomized. For example, if twenty codons are to be randomized at each position within an oligonucleotide population, then ten reaction vessels can be used. The use of a smaller number of reaction vessels than the number of codons to be randomized at each position is preferred because the smaller number of reaction vessels is easier to manipulate and results in a greater number of possible oligonucleotides synthesized.

Figure 2:
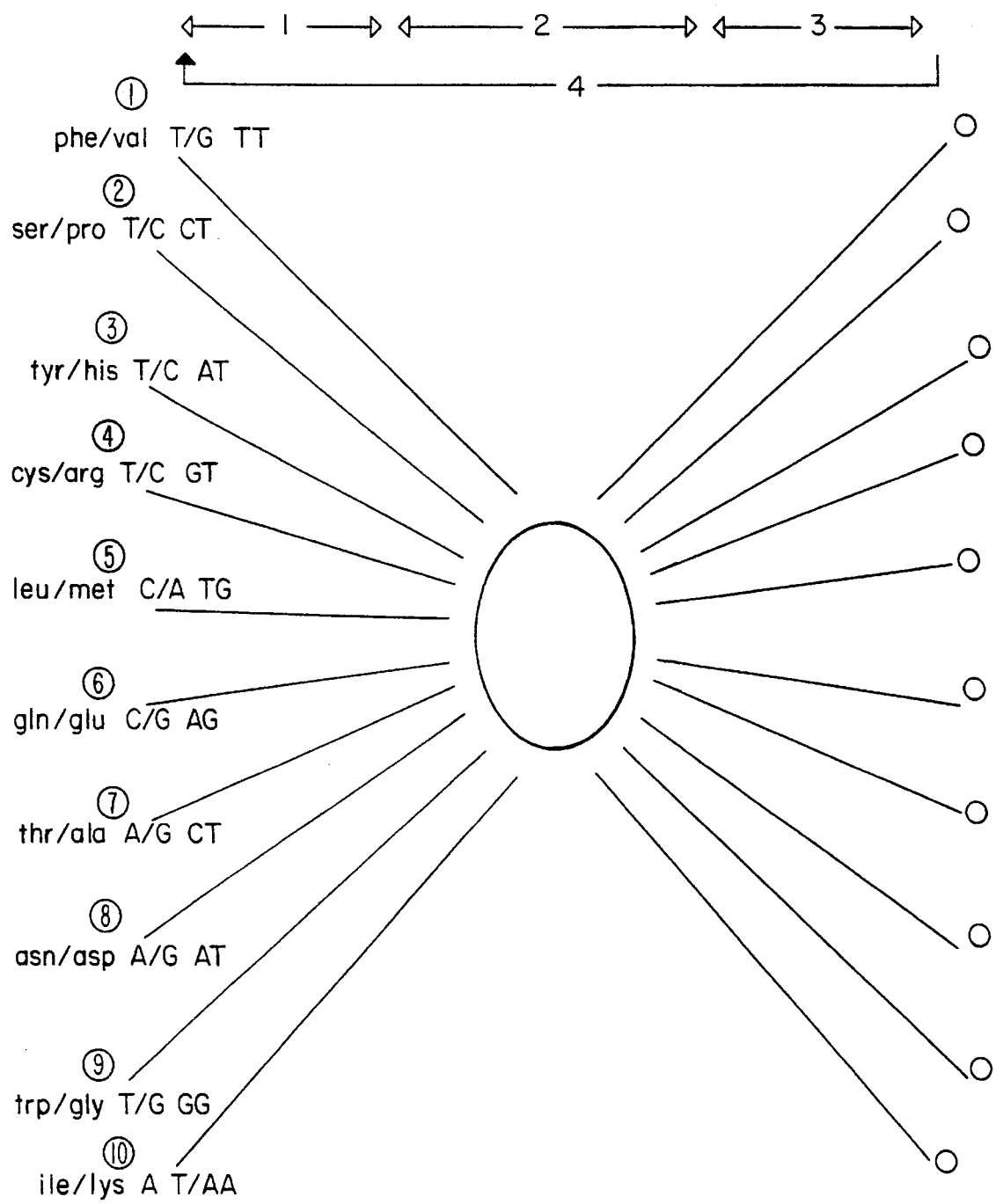
FIG. 2 is a schematic drawing for synthesizing oligonucleotides from nucleotide monomers with random tuplets at each position using ten reaction vessels.

The use of a smaller number of reaction vessels for random synthesis of twenty codons at a desired position within an oligonucleotide is similar to that described above using twenty reaction vessels except that each reaction vessel can contain the synthesis products of more than one codon. For example, step one synthesis using ten reaction vessels proceeds by coupling about two different codons on supports contained in each of ten reaction vessels. This is shown in FIG. 2 where each of the two codons coupled to a different support can consist of the following sequences: (1) (T/G)TT for Phe and Val; (2) (T/C)CT for Ser and Pro; (3) (T/C)AT for Tyr and His; (4) (T/C)GT for Cys and Arg; (5) (C/A)TG for Leu and Met; (6) (C/G)AG for Gln and Glu; (7) (A/G)CT for Thr and Ala; (8) (A/G)AT for Ash and Asp; (9) (T/G)GG for Trp and Gly and (10) A(T/A)A for Ile and Cys. The slash (/) signifies that a mixture of the monomers indicated on each side of the slash are used as if they were a single monomer in the indicated coupling step. The antisense sequence for each of the above codons can be generated by synthesizing the complementary sequence. For example, the antisense for Phe and Val can be AA(C/A). The amino acids encoded by each of the above pairs of sequences are given as the standard three letter nomenclature.

Coupling of the monomers in this fashion will yield codons specifying all twenty of the naturally occurring amino acids attached to supports in ten reaction vessels. However, the number of individual reaction vessels to be used will depend on the number of codons to be randomized at the desired position and can be determined by one skilled in the art. For example, if ten codons are to be randomized, then five reaction vessels can be used for coupling. The codon sequences given above can be used for this synthesis as well. The sequences of the codons can also be changed to incorporate or be replaced by any of the additional forty-four codons which constitutes the genetic code.

The remaining steps of synthesis of oligonucleotides with random codons using a smaller number of reaction vessels are as outlined above for synthesis with twenty reaction vessels except that the mixing and dividing steps are performed with supports from about half the number of reaction vessels. These remaining steps are shown in FIG. 2 (steps 2 through 4).

The invention also provides a method of synthesizing oligonucleotides using individual monomers having at least one specified tuplet at a predetermined position and the remaining positions having random tuplets. The synthesis steps are similar to those outlined above using twenty or less reaction vessels except that prior to synthesis of the specified codon position, the dividing of the supports into separate reaction vessels for synthesis of different codons is omitted. For example, if the codon at the second position of the oligonucleotide is to be specified, then following synthesis of random codons at the first position and mixing of the supports, the mixed supports are not divided into new reaction vessels but, instead, can be contained in a single reaction vessel to synthesize the specified codon. The specified codon is synthesized sequentially from individual monomers as described above. Thus, the number of reaction vessels can be increased or decreased at each step to allow for the synthesis of a specified codon or a desired number of random codons.

Following codon synthesis, the mixed supports are divided into individual reaction vessels for synthesis of the next codon to be randomized (FIG. 1, step 3) or can be used without separation for synthesis of a consecutive specified codon. The rounds of synthesis can be repeated for each codon to be added until the desired number of positions with predetermined or randomized codons are obtained.

Synthesis of oligonucleotides with the first position codon being specified can also be synthesized using the above method. In this case, the first position codon is synthesized from the appropriate monomers. The supports are divided into the required number of reaction vessels needed for synthesis of random codons at the second position and the rounds of synthesis, mixing and dividing are performed as described above.

The invention provides for a method of synthesizing oligonucleotides having tuplets which are diverse but biased toward a predetermined sequence. This method is advantageous to use when a significant number of codon positions, for example, are to be of a specified sequence since it alleviates the use of multiple reaction vessels. Instead, a mixture of four different monomers such as adenine, guanine, cytosine and thymine nucleotides are used for the first and second monomers in the codon. The codon is completed by coupling a mixture of a pair of monomers of either guanine and thymine or cytosine and adenine nucleotides at the third monomer position. Mixing of the two supports yields a population of oligonucleotides containing both the predetermined codon and the random codons at the desired position. Synthesis can proceed by using this mixture of supports in a single reaction vessel, for example, for coupling additional predetermined codons or, further dividing the mixture into two reaction vessels for synthesis of additional random codons.

The two reaction vessel method can be used for codon synthesis within an oligonucleotide with a predetermined tuplet sequence by dividing the support mixture into two portions at the desired codon position to be randomized. Additionally, this method allows for the extent of randomization to be adjusted. For example, unequal mixing or dividing of the two supports will change the fraction of codons with predetermined sequences compared to those with random codons at the desired position. Unequal mixing and dividing of supports can be useful when there is a need to synthesize random codons at a significant number of positions within an oligonucleotide of a longer or shorter length.

The extent of randomization can also be adjusted by using unequal mixtures of monomers in the first, second and third monomer coupling steps of the random codon position. The unequal mixtures can be in any or all of the coupling steps to yield a population of codons enriched in sequences reflective of the monomer proportions.

The invention provides for oligonucleotides synthesized by the methods described herein. Synthesis of randomized oligonucleotides is performed using methods well known to one skilled in the art. Linear coupling of monomers can, for example, be accomplished using phosphoramidite chemistry with a MilliGen/Biosearch Cyclone Plus automated synthesizer as described by the manufacturer (Millipore, Burlington, Mass.). Other chemistries and automated synthesizers can be employed as well and are known to one skilled in the art.

Synthesis of multiple codons can be performed without modification to the synthesizer by separately synthesizing the codons in individual sets of reactions. Alternatively, modification of an automated DNA synthesizer can be performed for the simultaneous synthesis of codons in multiple reaction vessels.

The following examples are intended to illustrate, but not limit the invention.

EXAMPLE I

Synthesis of an Oligonucleotide with Random Codons Using Individual Monomers

This example demonstrates the synthesis of an antisense oligonucleotide of ten codons in length with twenty random codons at each position.

The reaction vessels were obtained from the manufacturer of the automated synthesizer (Millipore, Burlington, Mass.; supplier of MilliGen/Biosearch Cyclone Plus Synthesizer) and were obtained as packages consisting of empty reaction columns (1 μmole), frits, crimps and plugs (MilliGen/Biosearch catalog # GEN 860458). Derivatized and underivatized control pore glass phosphoramidite nucleotides, and synthesis reagents were also obtained from MilliGen/Biosearch. Crimper and decrimper tools were obtained from Fisher Scientific Co., Pittsburgh, Pa. (Catalog numbers 06-406-20 and 06-406-25A, respectively).

Ten reaction columns are used for the synthesis of a ten codon random oligonucleotide. The oligonucleotide has 5 monomers at its 3' end of the sequence 5'GAGCT3' and 8 monomers at its 5' end of the sequence 5'AATTCCAT3'. The synthesizer is fitted with a column derivatized with a thymine nucleotide (MilliGen/Biosearch #0615.50) and is programmed to synthesize the sequences shown in Table I for each of ten columns in independent reaction sets. The sequence of the last three monomers (from right to left since synthesis proceeds 3' to 5') encode the indicated amino acids:

TABLE I

| Column | Sequence | Amino Acids |
| --- | --- | --- |
| column 1 | AA(A/C)GAGCT | Phe and Val |
| column 2 | AG(A/G)GAGCT | Ser and Pro |
| column 3 | AT(A/G)GAGCT | Tyr and His |
| column 4 | AC(A/G)GAGCT | Cys and Arg |

TABLE I-continued

| Column | Sequence | Amino Acids |
|---|---|---|
| column 5 | CA(G/T)GAGCT | Leu and Met |
| column 6 | CT(G/C)GAGCT | Gln and Glu |
| column 7 | AG(T/C)GAGCT | Thr and Ala |
| column 8 | AT(T/C)GAGCT | Asn and Asp |
| column 9 | CC(A/C)GAGCT | Trp and Gly |
| column 10 | T(A/T)TGAGCT | Ile and Cys | where the two monomers in parentheses denote a single monomer position within the codon and indicate that an equal mixture of each monomer is added to the reaction for coupling. The monomer coupling reactions for each of the 10 columns are performed as recommended by the manufacturer (amidite version S1.06, #8400-050990, scale 1 µM). After the last coupling reaction, the columns are washed with acetonitrile and lyophilized to dryness.

Following synthesis, the plugs are removed from each column using a decrimper and the reaction products are poured into a single weigh boat. Lost material is equalized with underivatized control pore glass and mixed thoroughly to obtain a random distribution of all twenty codon species. The reaction products are then aliquoted into 10 new reaction columns by removing 25 mg of material at a time and placing it into separate reaction columns. Alternatively, the reaction products can be aliquoted by suspending the beads in a liquid that is dense enough for the beads to remain dispersed, preferably a liquid that is equal in density to the beads, and then aliquoting equal volumes of the suspension into separate reaction columns. The lip on the inside of the columns where the frits rest are cleared of material using vacuum suction with a syringe and 25 G needle. New frits are placed onto the lips, the plugs are fitted into the columns and are crimped into place using a crimper.

Synthesis of the second codon position is achieved using the above 10 columns containing the random mixture of reaction products from the first codon synthesis. The monomer coupling reactions for the second codon position are shown in Table II. An A in the first position means that any monomer can be programmed into the synthesizer at that position since the first monomer position is not coupled by the synthesizer. An A also denotes that the columns from the previous codon synthesis should be placed on the synthesizer for use in the present synthesis round. Reactions are again sequentially repeated for each column as shown in Table II and described above, and the reaction products washed and dried.

TABLE II

| Column | Sequence | Amino Acids |
|---|---|---|
| column 1 | AA(A/C)A | Phe and Val |
| column 2 | AG(A/G)A | Ser and Pro |
| column 3 | AT(A/G)A | Tyr and His |
| column 4 | AC(A/G)A | Cys and Arg |
| column 5 | CA(G/T)A | Leu and Met |
| column 6 | CT(G/C)A | Gln and Glu |
| column 7 | AG(T/C)A | Thr and Ala |
| column 8 | AT(T/C)A | Asn and Asp |
| column 9 | CC(A/C)A | Trp and Gly |
| column 10 | T(A/T)TA | Ile and Cys |

Randomization of the second codon position is achieved by removing the reaction products from each of the columns and thoroughly mixing the material. The material is again divided into new reaction columns and prepared for monomer coupling reactions as described above.

Random synthesis of the next seven codons (positions 3 through 9) proceeds identically to the cycle described above for the second codon position and again used the monomer sequences of Table II. Each of the newly repacked columns containing the random mixture of reaction products from synthesis of the previous codon position is used for the synthesis of the subsequent codon position. After synthesis of the codon at position nine and mixing of the reaction products, the material is divided and repacked into 40 different columns and the monomer sequences shown in Table III are coupled to each of the 40 columns in independent reactions. The oligonucleotides from each of the 40 columns are mixed once more and cleaved from the control pore glass as recommended by the manufacturer.

TABLE III

| Column | Sequence |
|---|---|
| column 1 | AATTCCATAAAA |
| column 2 | AATTCCATAAAC |
| column 3 | AATTCCATAACA |
| column 4 | AATTCCATAACC |
| column 5 | AATTCCATAGAA |
| column 6 | AATTCCATAGAC |
| column 7 | AATTCCATAGGA |
| column 8 | AATTCCATAGGC |
| column 9 | AATTCCATATAA |
| column 10 | AATTCCATATAC |
| column 11 | AATTCCATATGA |
| column 12 | AATTCCATATGC |
| column 13 | AATTCCATACAA |
| column 14 | AATTCCATACAC |
| column 15 | AATTCCATACGA |
| column 16 | AATTCCATACGC |
| column 17 | AATTCCATCAGA |
| column 18 | AATTCCATCAGC |
| column 19 | AATTCCATCATA |
| column 20 | AATTCCATCATC |
| column 21 | AATTCCATCTGA |
| column 22 | AATTCCATCTGC |
| column 23 | AATTCCATCTCA |
| column 24 | AATTCCATCTCC |
| column 25 | AATTCCATAGTA |
| column 26 | AATTCCATAGTC |
| column 27 | AATTCCATAGCA |
| column 28 | AATTCCATAGCC |
| column 29 | AATTCCATATTA |
| column 30 | AATTCCATATTC |
| column 31 | AATTCCATATCA |
| column 32 | AATTCCATATCC |
| column 33 | AATTCCATCCAA |
| column 34 | AATTCCATCCAC |
| column 35 | AATTCCATCCCA |
| column 36 | AATTCCATCCCC |
| column 37 | AATTCCATTATA |
| column 38 | AATTCCATTATC |
| column 39 | AATTCCATTTTA |
| column 40 | AATTCCATTTTC |

EXAMPLE II

Synthesis of a Randomized Oligonucleotides with Predetermined Positions Having Specified Codons This example demonstrates the synthesis of a random oligonucleotide with the second position specifying the codon for methionine.

Synthesis of a random oligonucleotide having a specified codon at the second position is accomplished identically to that described in Example I except that the monomer sequence synthesized at the second position is identical for all ten reaction columns. The reaction columns containing the random codons, after the first position synthesis, are placed on the synthesizer and all ten columns receive the identical sequence of monomer coupling reactions. For methionine being the specified codon at the second position, the sequence is ATG. After all the coupling reactions are performed, the resultant product is a dinucleotide with the first position being random and the second position having a methionine codon. The columns are then used for the ten coupling reactions, as described in Example I to synthesize random codons at the remaining positions.

Although the invention has been described with reference to the presently preferred embodiment, it should be understood that various modifications can be made without departing from the spirit of the invention. Accordingly, the invention is limited only by the claims.

I claim:

1. A method of synthesizing oligonucleotides having random tuplets using individual monomers comprising the steps of:
   (1) sequentially coupling monomers on separate supports to form at least two different tuplets, said coupling being performed in separate reaction vessels;
   (2) mixing the supports from the separate reaction vessels;
   (3) dividing the mixed supports into two or more separate reaction vessels; and
   (4) repeating steps (1) through (3) one or more times in the reaction vessels of step (3), wherein the last step ends at step (2);
   wherein said tuplets are not triplet codons.

2. The method of claim 1 further comprising step (5) cleaving said oligonucleotides with random tuplets from said support.

3. The method of claim 1, wherein the number of tuplets to be randomized is between two and twenty.

4. The method of claim 1, wherein the number of reaction vessels is equal to the number of tuplets to be randomized.

5. The method of claim 4, wherein each tuplet to be randomized is coupled in a separate reaction vessel.

6. The method of claim 1, wherein the number of reaction vessels is less than the number of tuplets to be randomized.

7. The method of claim 6, wherein two tuplets to be randomized are coupled to a support in a reaction vessel.

8. A method of synthesizing oligonucleotides using individual monomers having at least one specified tuplet at a predetermined position and the remaining positions having random tuplets comprising the method of claim 1, wherein said specified tuplet position is synthesized on the mixed supports prior to dividing into separate reaction vessels.

9. The method of claim 8, wherein the first position is predetermined and the specified tuplet is synthesized prior to step (1).

10. A method of synthesizing oligonucleotides having tuplets which are diverse but biased toward a predetermined sequence comprising the steps of:
    (1) sequentially coupling monomers on a support to form a tuplet with a predetermined sequence, said coupling being performed in a first reaction vessel;
    (2) sequentially coupling monomers on a support to form a random tuplet, said coupling being performed in a second reaction vessel;
    (3) mixing the supports from said first and second reaction vessels; and
    (4) dividing the mixed supports from step (3) and using the supports in step (1) and step (2), wherein steps (1) through (3) are repeated at least once;
    wherein said tuplets are not triplet codons.

11. The method of claim 10 further comprising step (4) cleaving said oligonucleotide from said support.

12. The method of claim 10, wherein there are four different monomers adenine, guanine, cytosine and thymine.

13. The method of claim 12, wherein four different monomers in step 1, 2, 3, or 4 are present in equal proportions.

14. The method of claim 12, wherein the four different monomers in steps 1–4 are present in equal proportions.

15. The method of claim 12, wherein the four different monomers in steps 1–4 are present in unequal proportions.

16. The method of claim 12, wherein the four different monomers in steps 1–4 are present in unequal proportions.

17. The method of claim 12, wherein the guanine and thymine monomers of step 2 are present in equal proportions.

18. The method of claim 12, wherein the guanine and thymine monomers of step 2 are present in unequal proportions.

19. The method of claim 10, wherein the mixed supports from said first and second reaction vessels are divided into equal proportions.

20. The method of claim 10, wherein the mixed supports from said first and second reaction vessels are divided into unequal proportions.

* * * * *

UNITED STATES PATENT AND TRADEMARK OFFICE
CERTIFICATE OF CORRECTION

PATENT NO. : 5,523,388   Page 1 of 2
DATED : June 4, 1996
INVENTOR(S) : William D. Huse It is certified that error appears in the above-identified patent and that said Letters Patent is hereby corrected as shown below:

In the title, please delete "CODONS" and replace therefor with --TUPLETS--.

In column 1, line 6, please delete "08/071,1473" and replace therefor with --08/071,473--.

In column 1, line 6, please delete "which is" and replace therefor with --now--.

In column 1, line 8, please delete "(" and replace therefor with --issued as--.

In column 1, line 8, please delete ")".

In column 1, line 10, please delete "which is" and replace therefor with --now--.

In column 4, line 15, please delete "Will" and replace therefor with --will--.

In column 6, line 42, please delete "Ash" and replace therefor with --Asn--.

UNITED STATES PATENT AND TRADEMARK OFFICE
CERTIFICATE OF CORRECTION

PATENT NO. : 5,523,388
DATED : June 4, 1996
INVENTOR(S) : William D. Huse

It is certified that error appears in the above-identified patent and that said Letters Patent is hereby corrected as shown below:

In column 10, line 53, please delete "Oligonucleotides" and replace therefor with --Oligonucleotide--.

Signed and Sealed this

Ninth Day of June, 1998

Attest:

BRUCE LEHMAN

Attesting Officer          Commissioner of Patents and Trademarks